United States Patent [19]
Spurgeon

[11] 3,935,450
[45] Jan. 27, 1976

[54] APPARATUS AND METHOD FOR ALIGNING X-RAY DIFFRACTION CAMERA

[75] Inventor: A. Dale Spurgeon, Indianapolis, Ind.

[73] Assignee: Eli Lilly and Company, Indianapolis, Ind.

[22] Filed: July 12, 1974

[21] Appl. No.: 488,095

[52] U.S. Cl. ............... 250/273; 250/363; 250/491
[51] Int. Cl.² ........................................... G01N 21/00
[58] Field of Search .......... 250/252, 272, 273, 280, 250/491, 361, 362, 363, 369

[56] References Cited
UNITED STATES PATENTS
2,794,127   5/1957   Friedman ........................... 250/273

*Primary Examiner* — Davis L. Willis
*Attorney, Agent, or Firm* — Ralph W. Ernsberger; Everet F. Smith

[57] ABSTRACT

A device is described which is adaptable for use in aligning an X-ray diffraction camera to maximize the intensity of the X-rays contacting a substance undergoing diffraction analysis. Said device is comprised of an elongated housing adapted for placement in a port in said camera, a fluorescent material, such as β-zinc sulfide, disposed laterally within said housing, and a conductive photo-cell, such as a cadmium-selenide cell, disposed laterally in said housing immediately behind said fluorescent material. When such device is disposed in the camera port, X-rays entering said camera through an oppositely positioned port bombard said fluorescent material which fluoresces and excites said photo-cell. The resistance of such an excited photo-cell, changing inversely with the intensity of said fluorescence, is measured by passing electric current from an external source through said photo-cell.

The camera is aligned by adjusting it to the position where an ammeter indicates the maximum flow of such current.

12 Claims, 5 Drawing Figures

APPARATUS AND METHOD FOR ALIGNING X-RAY DIFFRACTION CAMERA

BACKGROUND OF THE INVENTION

1. Field of the Invention

This invention relates to a device for converting X-ray energy into resistance to the passage of a steady electric current and a method for utilizing such resistance to align an X-ray diffraction camera. More specifically this invention comprises a device which is adapted for use with an X-ray diffraction camera wherein a fluorescent material is disposed in said device in a position where X-rays entering said camera contact said fluorescent material, excite fluorescence therein which in turn excites a conductive photo-cell disposed adjacent to said fluorescent material wherein the resistance of said photo-cell to the passage of a steady electric current is altered and utilized to indicate the position of said camera, with respect to said X-rays, whereat the maximum intensity of said X-rays will contact a substance placed within said camera for X-ray diffraction analysis.

2. Prior Art

X-ray diffraction analysis of crystalline substances has been a recognized analytical tool for a long time. Such an analysis is highly useful for determining the degree or percentage of crystallinity of a substance or for measuring the sameness of the crystals in a sample which may be composed of more than one substance.

An X-ray diffraction camera is generally designed as a rather wide but shallow cylinder. The cylinder has two oppositely positioned ports in the sides thereof. A means is provided in the longitudinal center of the cylinder to place a small sample in a position that is both vertically and horizontally aligned with the two aforementioned ports. A means is provided to rotate said sample. The cylinder is closed on both ends, but the closure on one end is in the form of a door which can be opened and closed to position the sample and an unexposed photographic film in said cylinder. The photographic film is disposed around the interior perimeter of the cylinder.

In operation, the X-ray diffraction camera is positioned adjacent to a source of X-ray emission so that said X-rays can enter through one of the ports described above. The X-rays bombard the sample which is slowly rotated and are diffracted at an angle which is characteristic for the crystals being bombarded, and the X-rays contact the unexposed photographic film and cause an exposure of such film where the contact is made. Exposed film is compared with a standard film exposed from the bombardment of known crystals and an analysis can be computed therefrom.

In order to make full use of the precision and reliability of X-ray diffraction analysis it is important to maximize the intensity of the bombardment of each sample with direct (as contrasted with deflected) X-rays. The closer each sample comes to a uniform intensity, the greater the reliability and preciseness of the comparison of the X-ray diffraction pattern with a known standard.

In the past the X-ray diffraction camera has been aligned for maximum intensity of the X-rays contacting the sample by placing, in the port in the cylinder opposite the port through which the X-rays enter the camera, a device therein which comprises an elongated housing in which there is laterally disposed a fluorescent substance. Behind such fluorescent substance there is a piece of leaded glass through which the fluorescence of such substance can be observed. The room has been darkened, the X-ray generation begun and the camera manually manipulated to a position wherein the fluorescence has appeared to the eye to be the brightest. In practice it was found by consecutive analyses of identical samples that the adjustment of the intensity of the X-ray bombardment could vary as much as 60 percent when the same operator observed the brightness of the fluorescence. The result has been a loss in precision and reliability of the X-ray diffraction analyses.

Accordingly, it is an object of this invention to provide a device for quantitatively measuring the intensity of the direct X-rays to which a sample of material undergoing X-ray diffraction analysis is exposed in a diffraction camera, said device differentiating the relative intensity of such X-rays.

Another object of this invention is to provide a device which will convert X-ray energy to resistance to the passage of a steady electric current in a linear relationship in which the quantum of such resistance is inversely dependent upon the intensity of the X-rays entering the device.

Still another object of this invention is to provide a method for adjusting an X-ray diffraction camera in which the useful device described herein is utilized to maximize the intensity of the X-ray bombardment of a sample of material undergoing X-ray diffraction analysis in said camera.

SUMMARY

Now it has been discovered that by replacing the leaded glass in the device previously used to visually observe the fluorescence generated when X-rays contacted a fluorescent material with a conductive photo-cell positioned immediately adjacent to said material, and by measuring the resistance of the photo-cell by passing a steady electric current from an external source through said photo-cell, changes in the resistance of said photo-cell can be read out on an ammeter. The quantum of resistance being inversely proportional to the intensity of the X-rays striking the fluorescent material and exciting a fluorescence in said material, the highest reading on said ammeter at any steady current flow signifies a maximum intensity of X-rays entering said device. By adjusting the position of the X-ray diffraction camera in relation to the source of the X-rays as indicated by the maximum amperage observed assures the maximization of the X-ray intensity contacting the sample of material which is to undergo X-ray diffraction analysis.

DESCRIPTION OF THE PREFERRED EMBODIMENTS

In the following detailed description of the embodiments of this invention, reference is made to the accompanying drawings.

One embodiment of the instant invention is a device used in a method for aligning an X-ray diffraction camera. Such a device is comprised of: (a) A housing adapted to be disposed in a second port in an X-ray diffraction camera, said second port being located in said camera in the same horizontal and vertical planes as a first port through which X-rays enter said camera, said first and second ports being positioned at 180° from each other, said housing having a hollow tube which extends from the point of entry into the camera to a point adjacent to the vertical center line of said camera and a chamber axially positioned and cooperating with said tube and disposed external to said point of entry into said camera. (b) A fluorescent material disposed laterally in said chamber, said material extending across the diameter of said chamber immediately adjacent to the opening of said tube into said chamber. And, (c) a conductive photo-cell disposed in said chamber immediately adjacent to said fluorescent material and on the side thereof opposite to the opening of said tube into said chamber.

Figure 1:
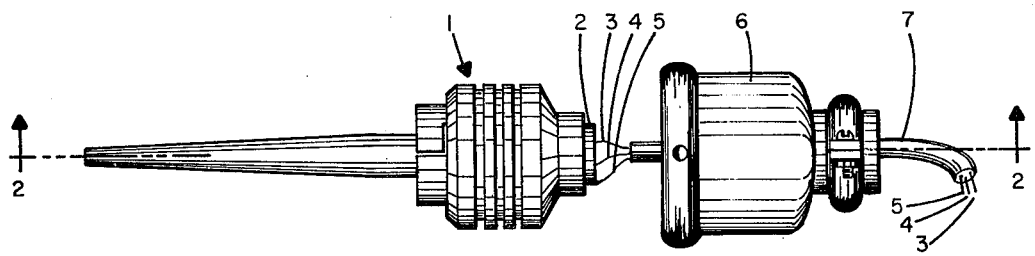
FIG. 1 is a top plan view of the partially disassambled device which converts X-ray energy to resistance to the passage of a steady electric current for use in focusing an X-ray diffraction camera.

Referring to FIG. 1, there is seen a partially disassembled device adapted for use in aligning an X-ray diffraction camera. The rendering shows a typical configuration. The housing 1 has an elongated tube to the left as the drawing is veiwed and a bulbous chamber on the right. The external flange of a photo-cell 2 is visible, and leads 3 and 4 from the photo-cell are shown exiting from the flange. A ground wire 5 is connected to the flange of the photo-cell. A cannon cap 6 is shown removed from the housing 1 to disclose the photo-cell 2 and the leads therefrom. The three-wire cable 7 is shown exiting from the cannon cap 6.

The cannon cap 6 constitutes no part of the instant invention as it is employed merely to protect the fragile leads from the photo-cell. The device performs the same without such protection.

Figure 2:
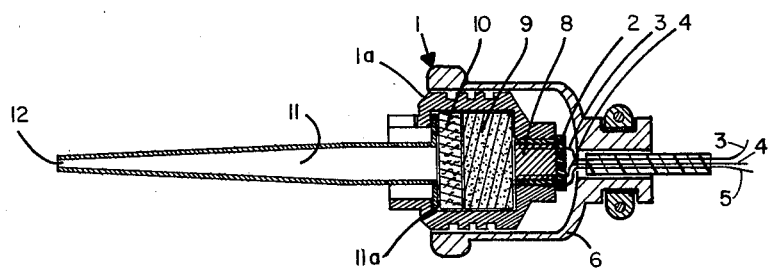
FIG. 2 is a cross-sectional view of the assembled device shown in FIG. 1.

This invention is more clearly seen in FIG. 2 which is a cross-sectional view of the device of FIG. 1 with the cannon cap in place.

The hollow tube 11 of the housing 1a is seen on the left, with an open end 12. In this illustration the hollow tube 11 is tapered, becoming increasingly larger in diameter as it advances from the opening 12 to its connection with the chamber 11a wherein there are disposed the fluorescent material 9 and the photo-cell element 8. Wadding 10 is disposed between the large end of the hollow tube 11 and the fluorescent material 9. The photo-cell is identified as 2, and the leads therefrom are shown as 3 and 4. The ground wire 5 and the cannon cap 6 complete the assembly.

The hollow tube 11 need not be tapered, but can be a simple cylinder. The tube 11 is designed to extend into the camera 16 (shown in FIGS. 4 and 5) to a point adjacent to the position in the camera where the sample which is to undergo X-ray diffraction analysis is placed. The diameter of tube 11 at the opening 12 should be about the same as the size of the sample to be placed in the camera after the focusing is completed. The extension of tube 11 into the camera avoids picking up scattered X-rays and consequently the X-rays reaching the fluorescent material are quantitatively about the same as will bombard the sample after the latter is placed in the camera.

The chamber 11a in which the fluorescent material and the photo-cell are disposed can be of any reasonable diameter and depth. The housing 1a shown in FIGS. 1 and 2 is similar to an existing prior art design utilized in visually aligning the camera.

The wadding 10 can be any material that is pervious to X-rays and unaffected by them. Filter paper is especially well-suited for use as wadding. Other wadding material which can be used include felt, both cotton and wool, synthetic fibers, both matted and woven, wood discs, such as balsa, and the like. The wadding serves to retain the fluorescent material 9 in the chamber 11a of housing 1a.

The fluorescent material 9 is generally a fine powder and is tightly packed in the chamber 11a. Larger particles such as small granules can be successfully employed, but powder is preferred. Among the fluorescent materials which are known to fluoresce when bombarded by X-rays are such well known substances as beta-zinc sulfide, cadmium tungstate, barium platinous cyanide, mesothorium, and tetracyanoplatinate, beta-zinc sulfide being preferred.

The conductive photo-cell 2 is disposed in the chamber 11a of housing 1a immediately adjacent to the fluorescent material and on the side thereof opposite the side receiving the X-ray bombardment. The element of the photo-cell 2 is shown as 8. The preferred element is cadmium-selenide. Other elements which would operate satisfactorily in this invention are cadmium sulfide and lead sulfide.

Those skilled in the art will recognize that light-sensitive electrical current generating elements can be adapted to the principle of this invention. Among these types are listed silicon or selenium photovoltaic cells and photo emissive photo sensors. And, photo-conductive junction-type cells can also be employed, but are not as sensitive as the photo-conductive bulk-type cells described herein. The spirit of the instant invention contemplates a scope which embraces all of these elements.

Exiting from the photo-cell 2 are electric current carrying leads 3 and 4, and a ground wire 5 which is attached to the casing of the photo-cell, which in turn is in intimate contact with housing 1a, proving a ground for the device.

In operation the X-rays which would bombard the sample undergoing X-ray diffraction analysis if such sample were in place in the camera enter tube 11 through opening 12 and travel the length of such tube. The X-rays leaving tube 11 penetrate the wadding 10 and are in part absorbed by the fluorescent material 9. On impingement with said material 9, such material fluoresces emitting optical energy. The degree of fluorescence is in direct proportion to the quantity of X-rays striking such material and consequently the quantity of optical energy produced is directly proportional to the quantity of X-rays which reach the fluorescent material. The photo-cell element is excited by the optical energy to which it is exposed, and the resistance of such element is altered inversely to the quantum of optical energy to which it is exposed. Passing a steady electric current through the photo-cell wherein the resistance varies with intensity of the optical energy provides a means for precisely and consistently aligning an X-ray diffraction camera to assure the concentration of the maximum quantity of X-rays on a sample unergoing analysis in such a camera.

Another embodiment of this invention comprises a method in which the device described hereinbefore is utilized in aligning an X-ray diffraction camera wherein the position of such a camera with respect to the source of X-rays is adjusted to concentrate the quantity of direct X-rays reaching a sample undergoing X-ray diffraction analysis in such camera to a maximum. Such a method is comprised of the following steps: (a) A device for converting X-ray energy to resistance to the passage of steady electric current is disposed in a second port in such camera, said second port being located in the same horizontal and vertical planes as a first port through which the X-rays enter such camera said first and second ports being positioned 180° from each other. Such a device is comprised of: (1) A housing adapted for disposing in said second port, said housing having a hollow tube extending from the point of entry into said camera to a point adjacent to the vertical center line of said camera, and a chamber axially positioned and cooperating with said tube and disposed external to said entry port. (2) A fluorescent material disposed laterally in said chamber, said material extending across the diameter of said housing. And, (3) a conductive photo-cell disposed in said chamber immediately adjacent to said fluorescent material and on the side thereof opposite to the opening of said tube into said chamber. (b) Said photo-cell is connected into a circuit wherein its resistance to the passage of steady electric current is indicated on an ammeter. (c) A stream of X-rays is introduced into said first port of said camera. (d) The fluorescent material in said device is contacted with said X-rays causing said material to fluoresce. (e) The fluorescence of said fluorescent material excites the element in said photo-cell. (f) The resistance of said photo-cell is varied inversely with changes in such fluoresence. (g) The inversely varying resistance of said photo-cell is indicated by passing a steady electric current therethrough and detecting variations in such resistance by deflections in an ammeter, said steady electric current being supplied from an external source. And, (h) the horizontal and vertical alignments of said camera are adjusted to a position where the minimum resistance to the passage of a steady electric current through said photo-cell is observed, such occurring when the maximum amperage is measured with no change in the steady electric current.

Figure 3:
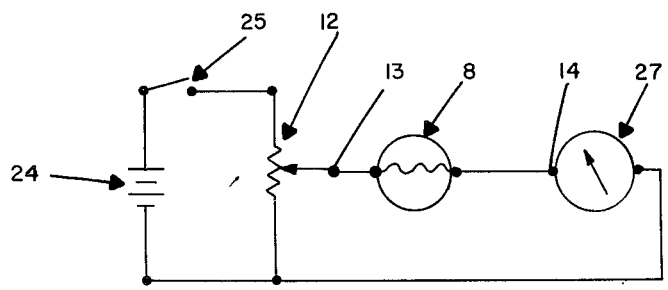
FIG. 3 is a schematic diagram of the circuitry utilized in the method for focusing an X-ray diffraction camera employing the device shown in FIG. 1.

The circuit into which the photo-cell is connected for the determination of the resistance thereof is shown in FIG. 3. The photo-cell element 8 is connected at 13 into a variable resistor 12 and into one side 14 of an ammeter 27. A source of electrical energy 24 is connected into said variable resistor and in parallel into the other pole of said ammeter 27. A switch 25 operates to close the circuit.

In operation, the photo-cell 8 is excited altering the resistance thereof. Switch 25 is closed and the variable resistor 12 is shunted so that a total current is flowing in the circuit sufficient to register about 50–75 percent of the scale of the ammeter 27. As the resistance of photo-cell element 8 changes the indication on the ammeter 27 moves to reflect such change, no modification of the setting of the variable resistor 12 being made.

If the initial setting of the variable resistor 12 was made when the resistance of the photo-cell element 8 was high, it may be necessary to re-set the variable resistor 12 to bring the ammeter 27 reading into the middle range on the scale.

The fluorescent material disposed in the device used in the novel method of this embodiment is selected from the same group as detailed hereinbefore. Again beta-zinc sulfide is the preferred material.

Similarly, the conductive photo-cell employed in this useful method can be selected from the group of elements detailed above, with the cadmium selenide element being perferred.

It was discovered that a 67½ volt battery was a convenient source of external electrical energy for use in this method and a variable resistor having a maximum resistance of 10,000 ohms worked well with such a battery.

Other voltages of direct current can be utilized and other variable resistors having different resistances can be combined with such alternate electrical energy sources to successfully operate the useful method of this embodiment. Those skilled in the art will know of such combinations.

With the battery source of direct current described above and the variable resistor associated therewith, a micro-ammeter is eminently satisfactory.

Figure 4:
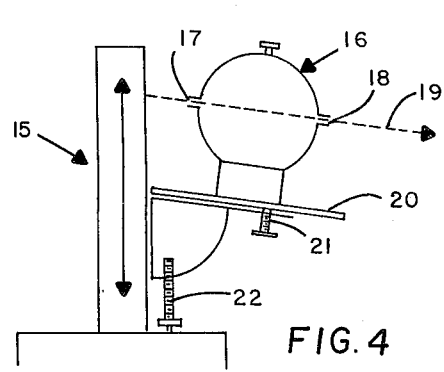
FIG. 4 is a profile view of the assembly of an X-ray diffraction camera and a source of X-rays.
Figure 5:
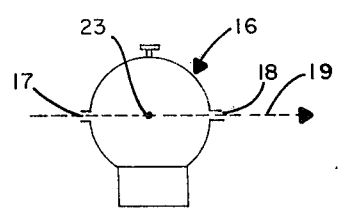
FIG. 5 is a profile view of an X-ray diffraction camera indicating the relative position of the sample undergoing analysis in relation to the beam of X-rays.

A profile of the arrangement and association between an X-ray source and an X-ray diffraction camera is shown in FIG. 4, and that of the camera above is detailed in FIG. 5.

The source of the X-rays is shown as 15. The X-ray diffraction camera is 16, and the first port therein is 17. The second port in such camera is 18, and the dashed line 19 illustrates the path of the X-ray emissions from 15 through port 17 and out port 18.

In FIG. 5, 23 locates the position where the sample is placed for X-ray diffraction analysis. The device 1 shown in FIG. 1 is disposed in port 18 shown in FIGS. 4 and 5. The hollow tube 11 extends into the camera 16 to a point adjacent to the position 23 of the sample.

The plate 20 on which camera 16 is disposed can be moved in three planes to effect alignment of said camera 16 to accommodate the maximum flow of X-rays into port 17 along the line 19. Adjustment bolt 22 raises and lowers the camera 16 in a vertical plane. Adjustment bolt 21 can be used to alter the inclination of the camera 16. An adjustment bolt (not shown) moves the camera 16 in a horizontal plane.

With the device 1 disposed in port 18 of camera 16 and X-ray emissions entering port 17, the horizontal, vertical and inclination adjustments are made to the position of the camera until the ammeter 27 reading is maximized at a particular setting of the variable resistor 12. When this is accomplished, the device 1 is removed from port 18, and an X-ray stop plug inserted therein. The camera 16 is then opened and the sample and film positioned therein, the camera closed and the X-ray diffraction conducted according to accepted procedures not a part of this invention.

What is claimed is:

1. A device for use in aligning an X-ray diffraction camera having first and second ports located in the same horizontal and vertical planes and positioned 180° from each other and a means for holding a sample for X-ray analysis disposed about midway between said ports and in axial alignment therewith comprising:
    a. a hollow tube adapted to be disposed in said second port, said hollow tube being designed to extend from the point of entry into said camera to a point adjacent to said sample holding means, and an axially disposed chamber connected to and cooperating with said tube and designed to be positioned externally to said camera when said tube is disposed therein;

b. a fluorescent material disposed in said chamber adjacent to said tube, said material being tightly packed completely across said chamber; and c. a conductive photo-cell disposed in said chamber immediately adjacent to said fluorescent material and on the side thereof opposite said tube.

2. The device of claim 1 wherein the fluorsecent material disposed within said chamber is selected from the group of such materials consisting of beta-zinc suflide, cadmium tungstate, barium platinous cyanide, mesothorium and tetracyanoplatinate.

3. The device of claim 1 wherein the fluorescent material disposed within said chamber is beta-zinc sulfide.

4. The device of claim 1 wherein the photo-cell disposed within said chamber is characterized as having an element selected from the group consisting of cadmium selenide, cadmium sulfide, and lead sulfide.

5. The device of claim 1 wherein the photo-cell disposed within said chamber is characterized as having a cadmium selenide element.

6. A method for aligning an X-ray diffraction camera having first and second ports located in the same horizontal and vertical planes and positioned 180° from each other and a means for holding a sample for X-ray analysis disposed about midway between said ports and in axial alignment therewith comprising the steps of disposing in said second port a device which converts X-ray energy to optical energy which in turn is utilized to inversely vary the resistance to the passage of steady electric current, said device comprising:

1. a hollow tube adapted to be disposed in said second port, said hollow tube being designed to extend from the point of entry into said camera to a point adjacent to said sample holding means, and an axially disposed chamber connected to and cooperating with said tube and designed to be positioned externally to said camera when said tube is disposed therein;

2. a fluorescent material disposed in said chamber adjacent to said tube, said material being tightly packed completely across said chamber, and 3. a conductive photo-cell disposed in said chamber immediately adjacent to said fluorescent material and on the side thereof opposite said tube;

b. connecting said photo-cell into an electrical circuit wherein variations in the resistance of said photo-cell is measured;

c. introducing a stream of X-rays into said first port of said camera;

d. contacting said fluorescent material with said X-rays causing said material to fluorence;

e. exciting said photo-cell with the fluorescence of said fluorescent material;

f. varying inversely the resistance of said photo-cell to the passage of a steady electric current as the fluorescence changes;

g. indicating the inversely varying resistance of said photo-cell on an ammeter; and h. adjusting the horizontal and vertical alignment of said camera with respect to said stream of X-rays to a position where the minimum resistance of said photo-cell to the passage therethrough of a steady electric current is observed when the maximum amperage is measured with no change in the steady electric current.

7. The method of claim 6 wherein the fluorescent material disposed in said chamber is selected from the group consisting of beta-zinc sulfide, cadmium tungstate, barium platinous cyanide, mesothorium, and tetracyanoplatinate.

8. The method of claim 6 wherein the fluorescent material is beta-zinc sulfide.

9. The method of claim 6 wherein the photo-cell disposed in said chamber is characterized as having an element selected from the group consisting of cadmium selenide, cadmium sulfide, and lead sulfide.

10. The method of claim 6 wherein the photo-cell is characterized as having a cadmium selenide element.

11. The method of claim 6 wherein the electrical circuit into which said photo-cell is connected is comprised of an external source of steady electric current, a variable resistor for modulating such current and an ammeter for measuring the current flowing in the circuit.

12. The method of claim 11 wherein the source of steady electric current is a 67½ volt battery, the variable resistor has a maximum resistance of 10,000 ohms, and the current is measured on a microammeter.

* * * * *